US012612406B2

(12) United States Patent
Clarke et al.

(10) Patent No.: US 12,612,406 B2
(45) Date of Patent: Apr. 28, 2026

(54) CYTISINE SALTS

(71) Applicant: Achieve Pharma UK Limited, Henley-on-Thomas (GB)

(72) Inventors: Anthony Clarke, Henley-on-Thomas (GB); Richard Alistair Balfour Stewart, Henley-on-Thomas (GB)

(73) Assignee: Achieve Life Sciences, Inc., Bothell, WA (US)

( * ) Notice: Subject to any disclaimer, the term of this patent is extended or adjusted under 35 U.S.C. 154(b) by 758 days.

(21) Appl. No.: 17/877,216

(22) Filed: Jul. 29, 2022

(65) Prior Publication Data

US 2022/0380369 A1      Dec. 1, 2022

Related U.S. Application Data

(62) Division of application No. 16/633,540, filed as application No. PCT/GB2018/052085 on Jul. 24, 2018, now Pat. No. 11,459,328.

(30) Foreign Application Priority Data

Jul. 24, 2017   (GB) ..................................... 1711899
Jul. 24, 2017   (GB) ..................................... 1711900

(51) Int. Cl.
| | |
|---|---|
| *C07D 471/18* | (2006.01) |
| *A61K 9/20* | (2006.01) |
| *A61K 9/48* | (2006.01) |
| *C07C 57/145* | (2006.01) |
| *C07C 65/05* | (2006.01) |
| *C07C 309/04* | (2006.01) |

(52) U.S. Cl.
CPC .......... *C07D 471/18* (2013.01); *A61K 9/2018* (2013.01); *A61K 9/2054* (2013.01); *A61K 9/2059* (2013.01); *A61K 9/4858* (2013.01); *A61K 9/4866* (2013.01); *C07C 57/145* (2013.01); *C07C 65/05* (2013.01); *C07C 309/04* (2013.01)

(58) Field of Classification Search
CPC .. C07D 471/18; A61K 9/2018; A61K 9/2054; A61K 9/2059; A61K 9/4858; A61K 9/4866; C07C 57/145; C07C 65/05; C07C 309/04
See application file for complete search history.

(56) References Cited

U.S. PATENT DOCUMENTS

2016/0199315 A1    7/2016  Takagi et al.

FOREIGN PATENT DOCUMENTS

| | | |
|---|---|---|
| CN | 101428021 | 5/2009 |
| EP | 1586320 | 10/2005 |
| EP | 0937077 | 5/2006 |
| GB | 2550241 | 11/2017 |
| JP | 2012512848 | 6/2012 |
| JP | 7178158 | 11/2022 |
| KR | 1020160019806 | 2/2016 |
| WO | 2014076680 | 5/2014 |
| WO | WO 2015/025718 | 2/2015 |
| WO | WO 2017/134468 | 8/2017 |

OTHER PUBLICATIONS

Gotti and Clementi, Cytisine and cytisine derivatives. More than smoking cessation aids Pharmacological Research vol. 170, Aug. 2021, 105700 (Year: 2021).*
International Search Report mailed Nov. 2, 2018, issued in corresponding International Application No. PCT/GB2018/052085, filed Jul. 24, 2018, 4 pages.
Written Opinion of the International Searching Authority mailed Nov. 2, 2018, issued in corresponding International Application No. PCT/GB2018/052085, filed Jul. 24, 2018, 6 pages.
U.K. Intellectual Property Office Search Report mailed Jan. 31, 2019, issued in corresponding Application No. GB1812071.7, 4 pages.
Chinese First Search Report issued in CN201880049384, dated Dec. 28, 2021, 1 page.
Chinese Supplementary Search Report issued in CN201880049384, dated Aug. 3, 2022, 1 page.
Kubicki, M et al., 'MS28-P7 Experimental deformation electron density studies of (-)-cytisine and its simply salts', Acta.Cryst., vol. A71, Aug. 23, 2015, p. s413-s414.
New Zealand Office Action issued in NZ76159618 dated May 27, 2025, 1-4 pages.
Rouden et al. ((-)-Cytisine and Derivatives: Synthesis, Reactivity, and Applications, Chem. Rev. 2014, 114, 712-778) (Year: 2014).
Stephenson, Charles Henry, and Charles Edwin Parker. Some Microchemical Tests for Alkaloids: Including Chemical Tests of the Alkaloids Used. JB Lippincott, 1921.

* cited by examiner

*Primary Examiner* — Adam C Milligan
*Assistant Examiner* — William Y Lee
(74) *Attorney, Agent, or Firm* — Sheppard Mullin Richter & Hampton L.L.P

(57) ABSTRACT

Salts of cytisine have been prepared and incorporated in stable pharmaceutical compositions, including compositions comprising lactose. The salts are prepared by adding acid stock solutions to solutions of cytisine with heating, followed by cooling to ambient temperature. The salts and compositions are indicated in the treatment of nicotine addiction.

12 Claims, 6 Drawing Sheets

CYTISINE SALTS

RELATED APPLICATIONS

This application is a continuation of U.S. patent application Ser. No. 16/633,540, filed on Jan. 23, 2020, which is a 371 U.S. National Stage Application of International Application No. PCT/GB2018/052085, entitled "CYTISINE SALTS," filed on Jul. 24, 2018, which claims the benefit of United Kingdom Patent Application Nos. 1711899.3, filed Jul. 24, 2017 and 1711900.9, filed on Jul. 24, 2017, which are hereby incorporated by reference herein in their entireties.

The present invention relates to novel salts of cytisine, processes for making them, pharmaceutical compositions containing them, and uses thereof.

BACKGROUND TO THE INVENTION

Cytisine is a pyridone-like alkaloid known to be a potent nicotinic acetylcholine receptor agonist. Pharmacologically, cytisine exhibits a high degree of similarity to nicotine. Numerous studies have indicated that cytisine is useful in the treatment of nicotine addiction.

A pharmaceutical smoking cessation product containing cytisine has been commercialised for several years under the brand name TABEX®. The TABEX® product is marketed in the form of an orally administered tablet comprising 1.5 mg of cytisine as a free base. While the product has been found to be efficacious and has been commercially successful, the approved shelf life of the product is two years.

As those skilled in the art will recognise, although a two-year shelf life for a pharmaceutical product is generally acceptable, it does impose pressure on the manufacturer and supply chain in terms of promptly packaging, transporting and delivering the product to users, and also increases the risk of stock wastage if the given shelf-life is exceeded. Additionally, where the product is to be shipped to territories with higher temperature or higher humidity climates (e.g. ICH climactic zones III and IV), then additional packaging or climate controls to protect the product and maintain shelf-life may be required.

A number of formulation approaches for cytisine-containing products are proposed in the prior art.

For example, EP1586320 discloses a solid dosage formulation of cytisine for oral administration. The formulation contains cytisine free base, lactose, microcrystal cellulose, talc powder, magnesium stearate and a film coating. Specific value ranges are given for the amount of cytisine and ratio of lactose:microcrystal cellulose, such compositions being said to provide tablets in which the active substance is evenly distributed. The results of stability tests are presented in the Examples. EP1586320 is concerned only with the free base of cytisine and does not consider cytisine salts.

WO2014/076680 relates to a solid dosage form in the form of a hard capsule comprising micronized cytisine and ancillary excipients. The formation of a homogeneous mass of powdered substances dosed into hard gelatine capsules containing a homogeneously dispersed active ingredient, prepared without the use of increased moisture and temperature is said to ensure cytisine stability throughout the technological process. WO2014/076680 discusses incompatibility between the cytisine active ingredient and lactose, and states that lactose may destabilise tablets comprising cytisine due to the presence of a carboxyl group in the lactose molecule, which is not completely inert chemically and may lead to a Maillard reaction. Salts of cytisine are not considered.

The succinate salt of cytisine is known from WO2017/134468. The salt may be formulated into a stable pharmaceutical composition comprising the succinate salt of cytisine and a pharmaceutically acceptable carrier which may be, for example, lactose monohydrate or anhydrous lactose. Improved stability of such compositions over compositions of cytisine free base and lactose is demonstrated.

The formation of salts of cytisine is known to be challenging, and no commercial formulations containing salts of cytisine are currently available. As demonstrated below, Cytisine does not form stable salts with common salt formers, such as acetic and benzoic acid, as demonstrated below. Surprisingly, however, the present inventors have found that stable salts of cytisine may be achieved when the salt is selected from a mesylate salt of cytisine; a gentisate salt of cytisine; and a maleate salt of cytisine. Such stable salts present additional options for formulating cytisine into stable pharmaceutical compositions.

DISCLOSURE OF THE INVENTION

According to a first aspect of the present invention, there is provided a salt of cytisine selected from a mesylate salt of cytisine; a gentisate salt of cytisine; and a maleate salt of cytisine. Such salts may be formulated with lactose or other common pharmaceutical carriers to provide compositions for use in therapy, for example, in the treatment of nicotine addiction.

The salts of the present invention are crystalline salts.

In embodiments of the present invention, the mesylate, gentisate, or maleate salt of cytisine may be present in the form of a solvate or a hydrate.

In a second aspect of the present invention, there is provided a process for making a salt of cytisine selected from a mesylate salt of cytisine, a gentisate salt of cytisine, and a maleate salt of cytisine, comprising:

(i) preparing a first solution, of an acid salt former selected from methanesulphonic acid, gentisic acid, and maleic acid;

(ii) preparing a second solution, of cytisine;

(iii) adding said solution of an acid salt former to said solution of cytisine;

(iv) maintaining the solution obtained in step (iii) at an elevated temperature for a fixed period of time;

(v) allowing the solution to cool to ambient temperature;

(vi) filtering the cooled solution; and (vii) drying the obtained solids.

In the process of the invention, the first solution, of an acid salt former, may be provided for example by mixing the acid salt former in a suitable solvent, such as ethanol or a mixture of ethanol and water, for example. The second solution, of cytisine, may be prepared by dissolving cytisine in a suitable solvent, such as acetonitrile, or methyltetrahydrofuran, for example. Dissolution may be achieved by heating the solvent, for example to a temperature of 40-60° C., or by any other suitable method as will be known by the person skilled in the art. Once mixed in accordance with step (iii) above, the obtained solution may be maintained at an elevated temperate of, for example, around 40° C., for a time period of, for example, around one hour. After cooling, filtration of the obtained solids may be carried out, for example using a PTFE fritted column, and the obtained solids are then dried at a suitable temperature, for example at a temperature of around 50° C., for a suitable period of time, for example a period of time of around 48 hours.

The salts obtained in the above process may be further processed by known means, before being included in a pharmaceutical composition. For example, the salts may be micronized or otherwise processed.

According to a third aspect of the present invention, there is provided a pharmaceutical composition comprising a salt of cytisine selected from a mesylate salt of cytisine, a gentisate salt of cytisine, and a maleate salt of cytisine, and a pharmaceutically acceptable carrier.

Pharmaceutical carriers are well known in the art. For example, lactose is commonly used in solid dosage formulations. In an embodiment, the pharmaceutically acceptable carrier in the compositions of the present invention is lactose. The lactose may be, for example, lactose monohydrate or anhydrous lactose. Alternative carriers include cellulose, for example microcrystalline cellulose, or starch, for example corn starch and/or wheat starch.

Pharmaceutical compositions including cytisine salts in accordance with the present invention may have improved stability, for example in pharmaceutical compositions, and particularly in pharmaceutical compositions comprising lactose, compared with known compositions comprising cytisine free base.

The compositions disclosed herein may be suitable for administration by any route known in the art. Pharmaceutical compositions encompassed within this aspect of the invention include those suitable for oral, nasal or topical administration. In an embodiment, the composition may be formulated in a solid form such as a tablet or a capsule for oral administration.

The compositions of the present invention may additionally contain one or more excipients, such as are common in the art. Excipients that may be employed in the compositions of the present invention include, for example, fillers, disintegrants, preserving agents, lubricants and wetting agents.

Examples of fillers that may be used include lactose (for example, either anhydrous or monohydrate), cellulose, starch (for example, corn and/or wheat starch), calcium phosphates, calcium sulphates, and mannitol.

Preserving agents prevent bacterial or fungal contamination of the formulation and may include various antibacterial and antifungal agents such as parabens, chlorobutanol, phenol, and sorbic acid.

Suitable lubricants include stearic acid and its salts. One example of a lubricant for use in the compositions of the present invention is magnesium stearate.

The pharmaceutical compositions of the invention may further comprise sweetening, flavouring or colouring agents.

The skilled person will be well aware of suitable fillers, preserving agents and lubricants other than those specifically mentioned above, as well as suitable sweetening, flavouring, and colouring agents and other additives The pharmaceutical compositions of the present invention may comprise a coating, for example a film coating, and may be coated according to any method known in the art, for example using collidine, shellac, gum arabic, talc, titanium dioxide, or sugar.

Pharmaceutical compositions in accordance with the present invention may be prepared by any suitable method. For example, capsules may be prepared by mixing the salt with one or more inert carriers such as lactose or sorbitol and packing into gelatine capsules. Tablets may be made by known compression methods, for example.

In embodiments of the invention, the pharmaceutical composition will be provided as a unit dosage form (e.g. a tablet or capsule). The amount of cytisine in the composition may range from about 0.5 mg or about 1.0 mg to 2.0 mg, 3.0 mg, 5.0 mg or about 10 mg. For example, a unit dosage form may comprise 1 to 3.5 mg of the salt. In embodiments, the pharmaceutical compositions of the present invention may have a shelf life greater than 2 years when stored at 25° C. and at a relative humidity of 60%±5%.

The salts and pharmaceutical compositions of the present invention are indicated for example for use in the treatment of nicotine addiction.

Thus, in a fourth aspect of the invention, there is provided a salt of cytisine selected from a mesylate salt of cytisine, a gentisate salt of cytisine, and a maleate salt of cytisine, for use in the treatment of nicotine addiction, and a pharmaceutical composition comprising a salt of cytisine selected from a mesylate salt of cytisine, a gentisate salt of cytisine, and a maleate salt of cytisine, and a pharmaceutically acceptable carrier, for use in the treatment of nicotine addiction.

In a fifth aspect of the present invention, there is provided a method of treating nicotine addiction in a subject, said method comprising administering to said subject an effective amount of a salt of cytisine selected from a mesylate salt of cytisine, a gentisate salt of cytisine, and a maleate salt of cytisine.

FIGURES

The various embodiments of the present invention will now be further explained with reference to the following examples.

EXAMPLES

Example 1—Salt Formation

Stock solutions of acid salt formers were prepared in the carrier solvents and having the molarities detailed in the following Table 1 below:

TABLE 1

| List of acid solution for screening cytisine salt formation | | |
| --- | --- | --- |
| Acid | Solvent mix | Molarity |
| Acetic | EtOH | 1 |
| Ascorbic | 9:1 EtOH:Water | 0.5 |
| Benzoic | EtOH | 1 |
| Gentisic | EtOH | 0.5 |
| Glucuronic | Water | 0.5 |
| Maleic | EtOH | 1 |
| Methansulphonic | EtOH | 1 |

Stock solutions of cytisine API (non-synthetic) were also prepared in $CH_3CN$ and in Me-THF. 2.4 g of cytisine was dissolved in 60 ml of 2-Me-THF heated to a temperature of 60° C. 2.4 g of cytisine was dissolved in 24 ml of $CH_3CN$ heated to a temperature of 40° C.

200 ml capacity tubes heated to 40° C. were charged with 2 ml or 5 ml of the cytisine stock solution. The acid stock solutions were then added to the heated tubes in equimolar amounts. The solutions were held at 40° C. for one hour and then allowed to cool to ambient temperature (~18° C.) for 18 hours. Where solid formation did not spontaneously occur, successive secondary manipulations were carried out in order to induce crystallisation, namely: i) gradual blow down under nitrogen to induce crystallisation, ii) charging antisolvent/triturate, and iii) second blow down under nitrogen and trituration with 3 ml TBME and 1 ml acetone.

Filtration of the obtained solids was then carried out using a PTFE fritted column and the obtained solids were dried at 50° C. for 48 hours. The properties of the obtained products were then analysed, and the outcome of this screen and the properties of the obtained products are summarised in Table 2 below:

TABLE 2

Salt preparation

| API Stock Solution | Salt-type | Assessment |
|---|---|---|
| CH₃CN | Acetate | Secondary precipitations, unstable salt |
| 2-MeTHF | Acetate | Secondary precipitations, unstable salt |
| CH₃CN | Ascorbate | Secondary precipitations, unstable salt |
| 2-MeTHF | Ascorbate | Secondary precipitations, unstable salt |
| CH₃CN | Benzoate | Failed to yield solid |
| 2-MeTHF | Benzoate | Failed to yield solid |
| CH₃CN | Gentisate | Excellent salt profile |
| 2-MeTHF | Gentisate | Excellent salt profile |
| CH₃CN | Glucuronate | Failed to yield solid |
| 2-MeTHF | Glucuronate | Failed to yield solid |
| CH₃CN | Maleate | Excellent salt profile |
| 2-MeTHF | Maleate | Excellent salt profile |
| CH₃CN | Mesylate | Excellent salt profile |
| 2-MeTHF | Mesylate | Excellent salt profile |

As can be seen, suitable salts could not be formed with the common acid salt formers acetic acid and benzoic acid, as well as with the more exotic salt formers ascorbic acid and glucoronic acid. However, the mesylate, gentisate, and maleate salts were readily formed, exhibiting advantageous properties.

Example 2—Characterisation Tests

Figure 1:
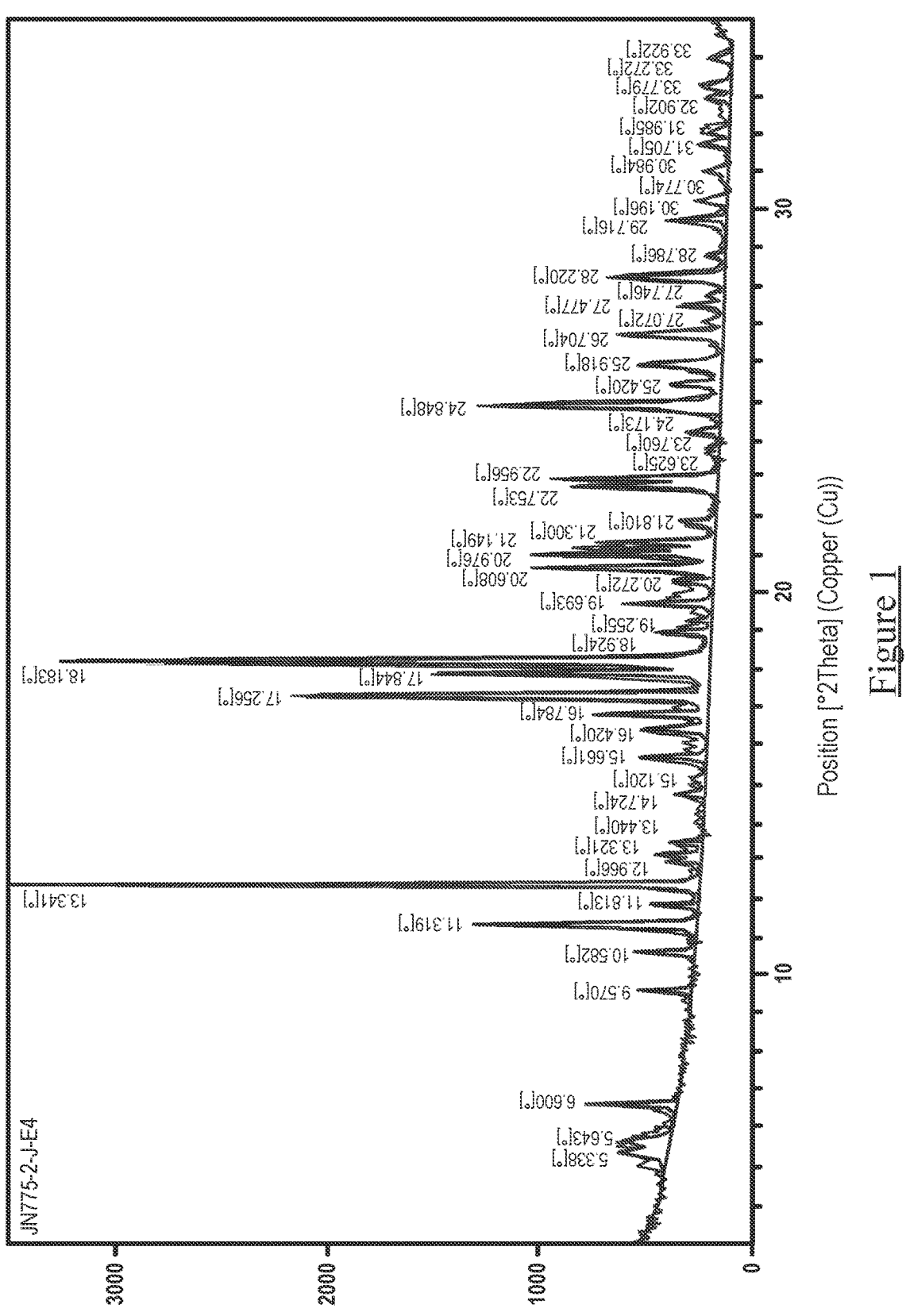
FIG. 1 shows the XRPD profile for cytisine mesylate.
Figure 2:
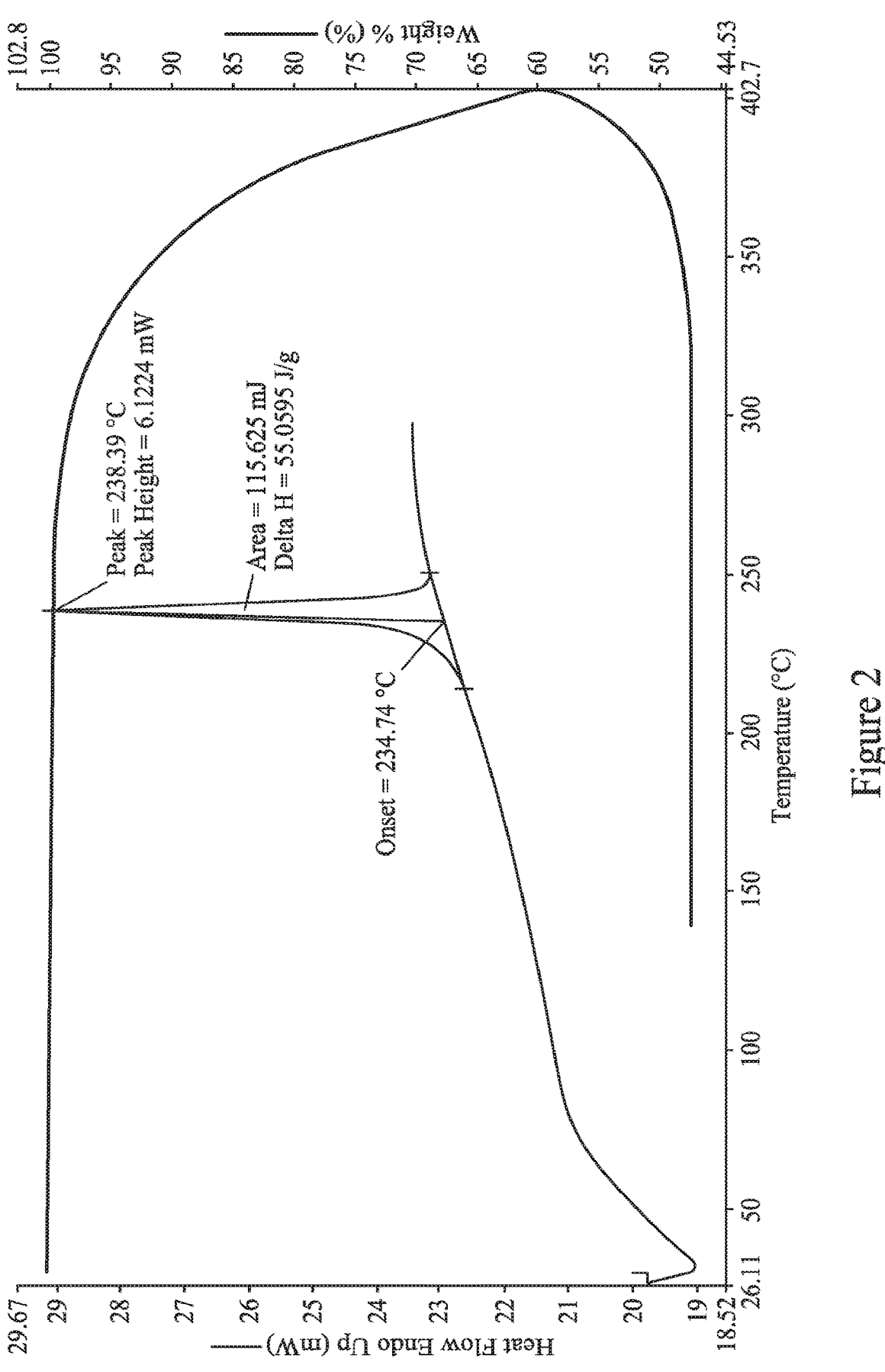
FIG. 2 shows the combined DSC/TGA profile for cytisine mesylate.
Figure 3:
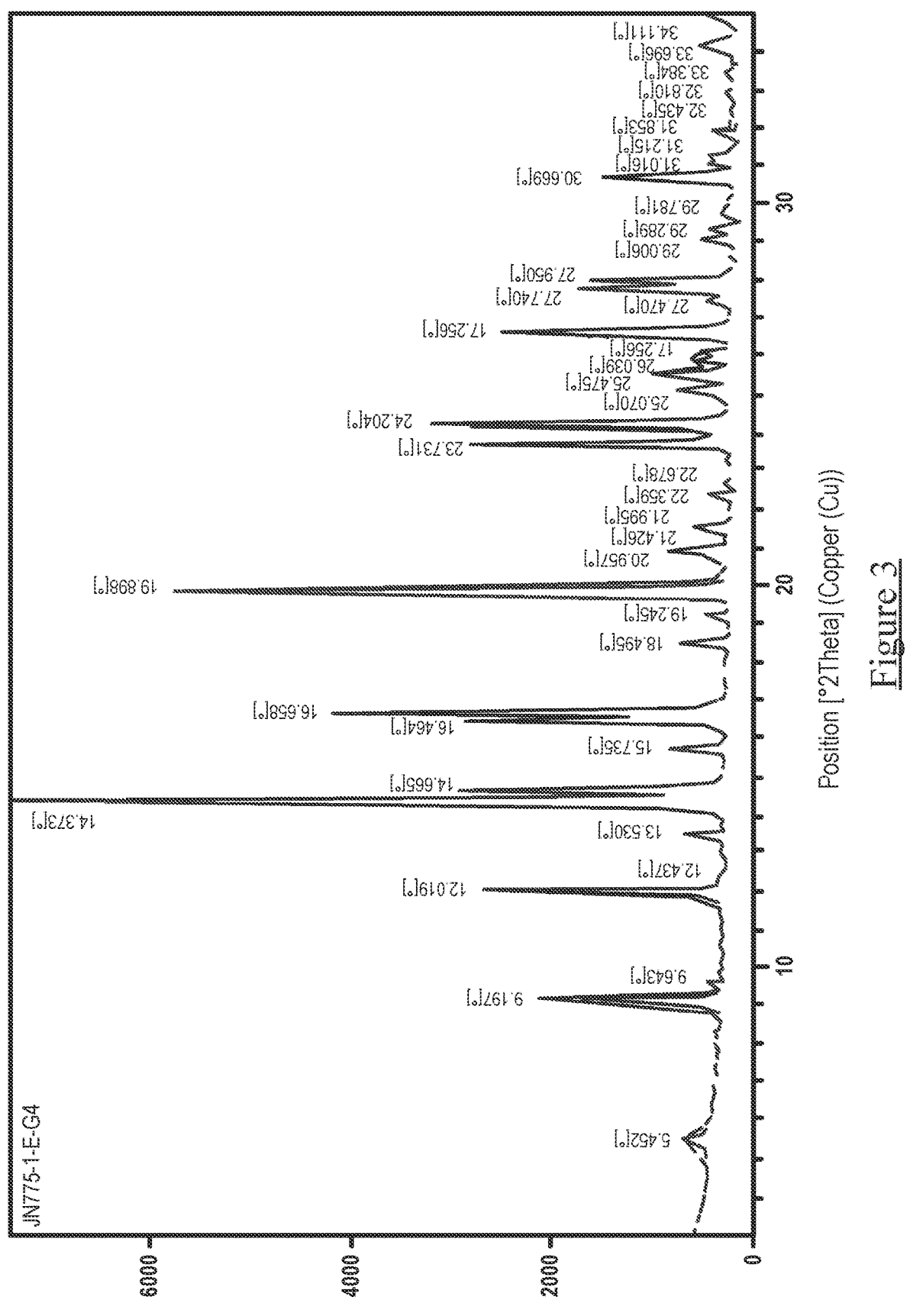
FIG. 3 shows the XRPD profile for cytisine gentisate.
Figure 4:
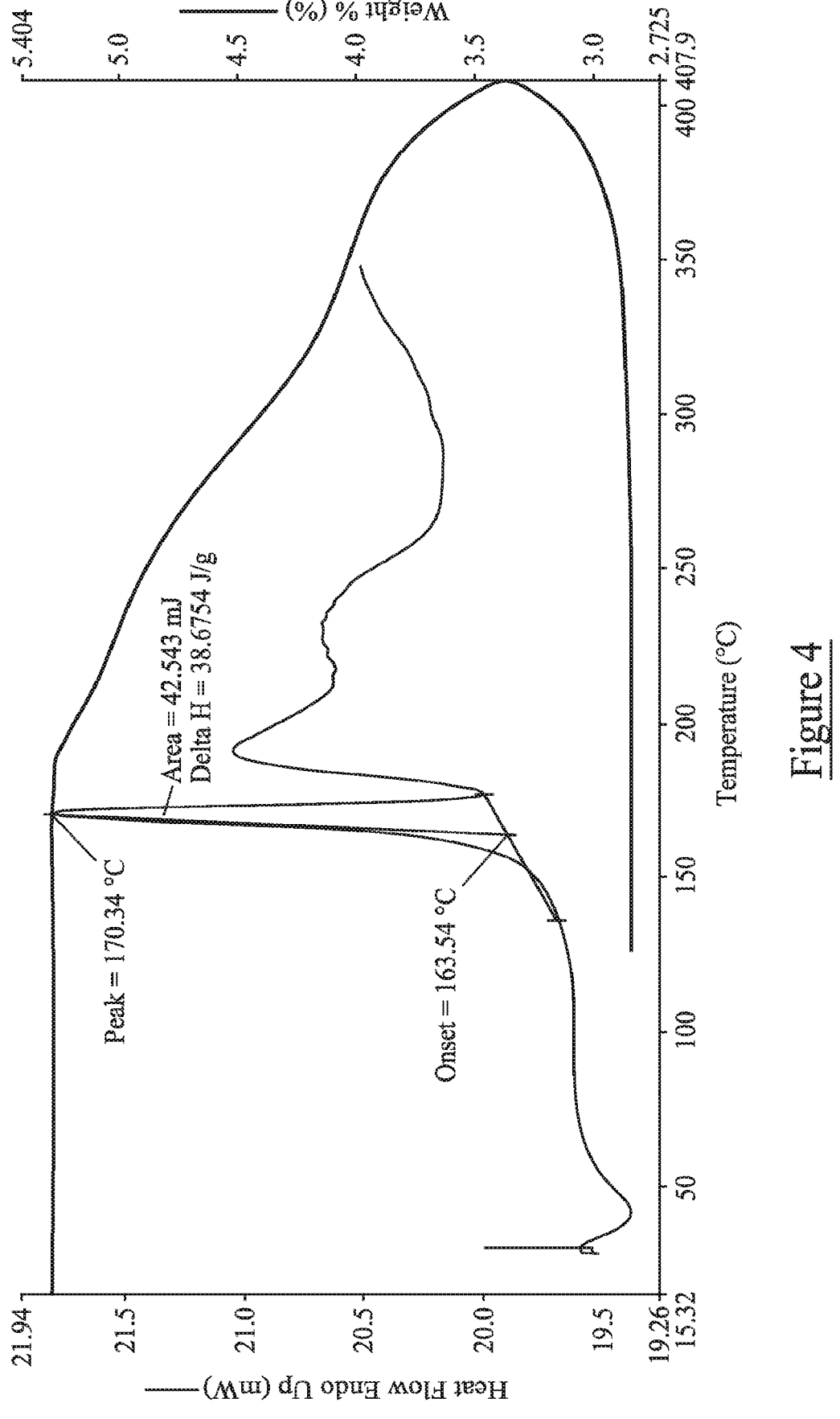
FIG. 4 shows the combined DSC/TGA profile for cytisine gentisate.
Figure 5:
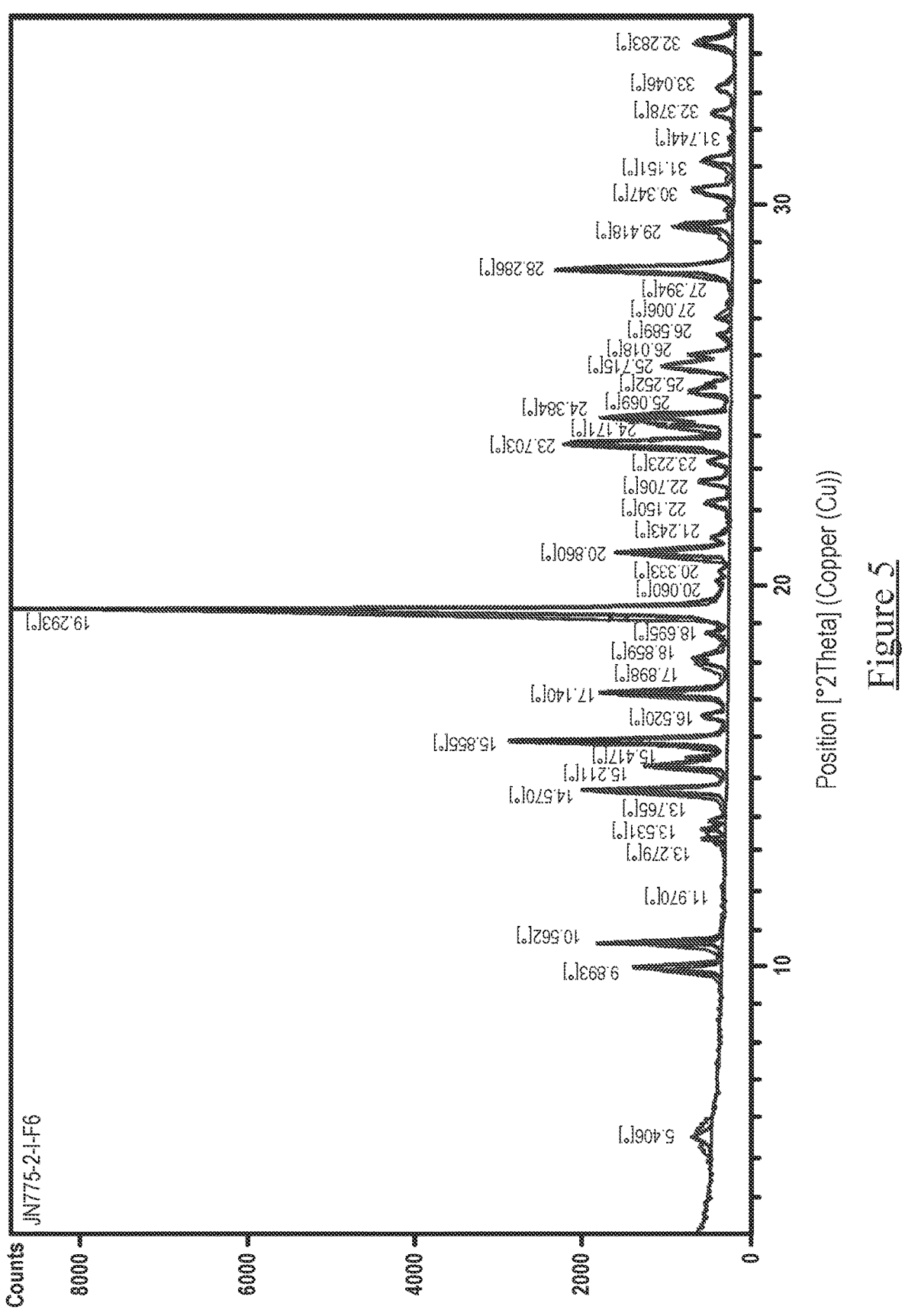
FIG. 5 shows the XRPD profile for cytisine maleate.
Figure 6:
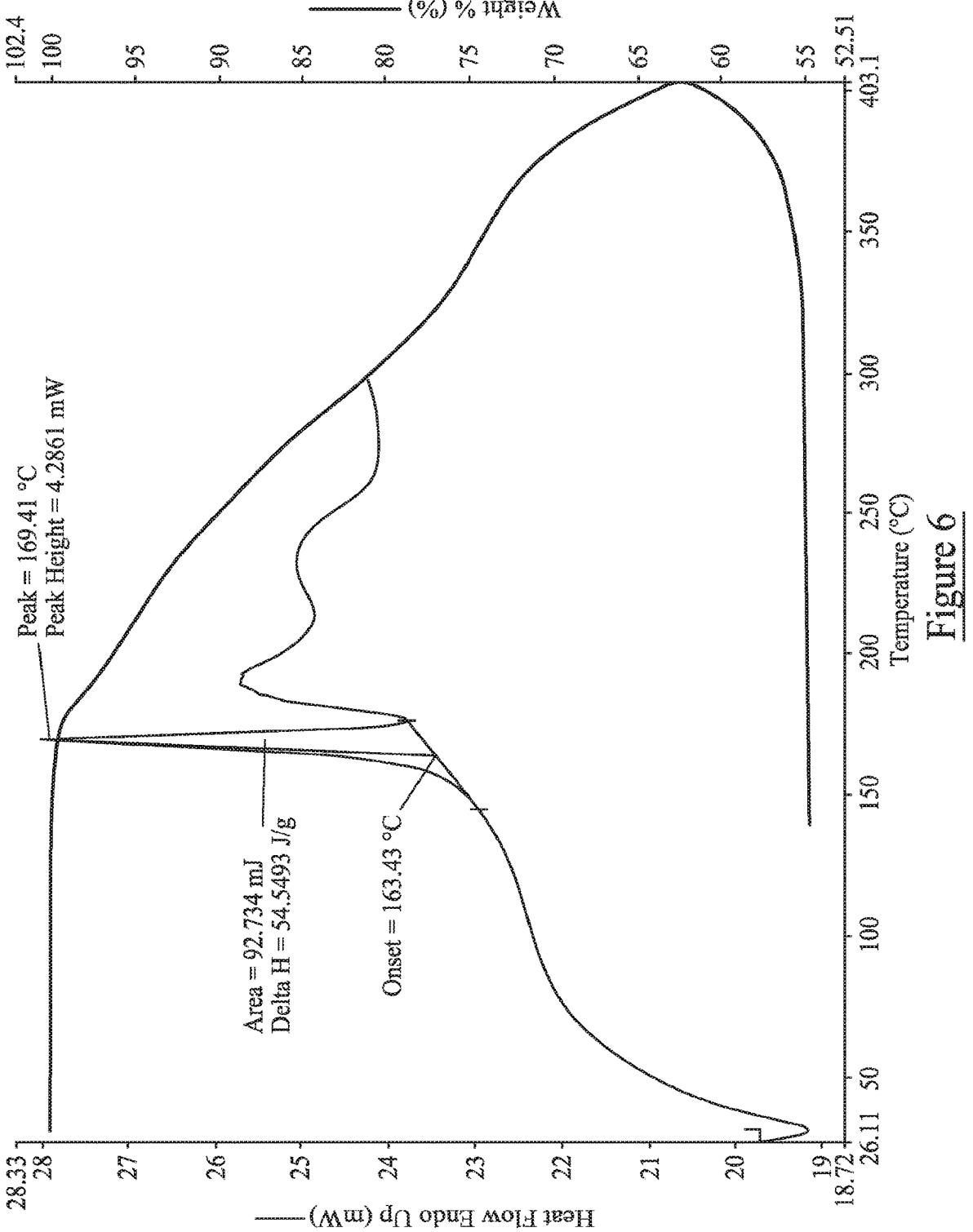
FIG. 6 shows the combined DSC/TGA profile for cytisine maleate.

The obtained salts were subjected to XRPD, DSC and TGA analysis, using the apparatus and parameters outlined below. The results are presented in Tables 3-5 below and illustrated in FIGS. 1-6 as described above.
X-Ray Powder Diffraction (XRPD)

X-Ray Powder Diffraction patterns were collected on a PANalytical™ diffractometer using Cu Kα radiation (45 kV, 40 mA), θ-θ goniometer, focusing mirror, divergence slit (½"), soller slits at both incident and divergent beam (4 mm) and a PIXcel™ detector.

The software used for data collection was X'Pert™ Data Collector, version 2.2f and the data was presented using X'Pert™ Data Viewer, version 1.2d.

XRPD patterns were acquired under ambient conditions via a transmission foil sample stage (polyimide—Kaplan, 12.7 μm thickness film) under ambient conditions using a PANalytical™ X'Pert™ PRO. The data collection range was 2.994-35°2θ with a continuous scan speed of 0.202004°s−1.
Differential Scanning Calorimetry (DSC)

DSC data was collected on a PerkinElmer Pyris™ 6000 DSC equipped with a 45 position sample holder. The instrument was verified for energy and temperature calibration using certified indium. A predefined amount of the sample, 0.5-3.0 mg, was placed in a pin holed aluminium pan and heated at 20° C.min−1 from 30 to 350° C., or varied as experimentation dictated. A purge of dry nitrogen at 20 ml·min-1 was maintained over the sample. The instrument control, data acquisition and analysis were performed with Pyris™ Software v11.1.1 Revision H.
Thermo-Gravimetric Analysis (TGA)

TGA data were collected on a PerkinElmer Pyris™ 1 TGA equipped with a 20 position auto-sampler. The instrument was calibrated using a certified weight and certified Alumel and Perkalloy for temperature. A predefined amount of the sample, 1-5 mg, was loaded onto a pre-tared aluminium crucible and was heated at 20° C.min−1 from ambient temperature to 400° C. A nitrogen purge at 20 ml·min−1 was maintained over the sample.

The instrument control, data acquisition and analysis were performed with Pyris™ Software v11.1.1 Revision H.

TABLE 3

Cytisine Mesylate Characterization

| Properties | Cytisine Mesylate |
|---|---|
| XRPD | Crystalline. Peaks at: 5.3, 5.6, 6.6, 9.6, 10.6, 11.3, 11.8, 12.3, 13.0, 13.4, 14.7, 15.1, 15.7, 16.4, 16.8, 17.3, 17.8, 18.2, 18.9, 19.3, 19.7, 20.3, 20.6, 21.0, 21.3, 21.8, 22.8, 23.0, 23.6, 23.8, 24.2, 24.8, 25.4, 25.9, 26.7, 27.0, 27.5, 27.7, 28.2, 28.8, 29.7, 30.2, 30.8, 31.0, 31.7, 32.0, 32.9, 33.2, 33.3, 33.9 2θ |
| DSC | Sharp endotherm at 238° C. |
| TGA | Decomposition from 238° C. |

TABLE 4

Cytisine Gentisate Characterization

| Properties | Cytisine Gentisate |
|---|---|
| XRPD | Crystalline, Peaks at: 5.5, 9.2, 9.6, 12.0, 12.4, 13.5, 14.4, 14.7, 15.7, 16.5, 16.7, 18.5, 19.2, 19.9, 21.0, 21.4, 21.6, 22.4, 22.7, 23.7, 24.2, 25.1, 25.5, 25.9, 26.1, 26.6, 27.5, 27.7, 28.0, 29.0, 29.3, 29.8, 30.7, 31.0, 31.2, 31.9, 32.4, 32.8, 33.4, 33.7, and 34.1 2θ |
| DSC | Sharp endotherm at 230° C. |
| TGA | Decomposition from 230° C. |

TABLE 5

Cytisine Maleate Characterization

| Properties | Cytisine Maleate |
|---|---|
| XRPD | Crystalline. Peaks at: 5.4, 9.9, 10.6, 12.0, 13.3, 13.6, 13.8, 14.6, 15.2, 15.4, 15.9, 16.6, 17.1, 17.9, 18.1, 18.7, 19.3, 20.1, 20.3, 20.9, 21.2, 22.2, 22.7, 23.2, 23.7, 24.2, 24.4, 25.1, 25.3, 25.7, 26.0, 26.6, 27.0, 27.4, 28.3, 29.4, 30.3, 31.2, 31.8, 32.4, 33.0 and 34.3 2θ |
| DSC | Sharp endotherm at 169° C. |
| TGA | Decomposition from 169° C. |

Example 3—Lactose Compatibility

The stability of formulations of cytisine and the present cytisine salts with lactose was investigated. Samples were stored at 25° C. and 60% relative humidity (RH) and at 40° C. and 75% RH and evaluated after 7 and 14 days. As can be seen from the data in Tables 6 and 7, when present in the form of its mesylate or gentisate salt, cytisine is degraded at a substantially lower rate than when present in free base form. Thus, these salts effectively improve the stability of cytisine and facilitates its formulation with compositions comprising lactose.

TABLE 6

Stability evaluation of cytisine salts in the presence
of lactose following storage at 25° C. and 60% RH:

| Formulation | Cytisine by HPLC, area % - 7 days | Cytisine by HPLC, area % - 14 days |
|---|---|---|
| Cytisine with lactose | 98.77 | 94.99 |
| Cytisine mesylate with lactose | 99.54 | 99.66 |
| Cytisine gentisate with lactose | 97.98 | 98.37 |

TABLE 7

Stability evaluation of cytisine salts in the presence
of lactose following storage at 40° C. and 75% RH:

| Formulation | Cytisine by HPLC, area % - 7 days | Cytisine by HPLC, area % - 14 days |
|---|---|---|
| Cytisine with lactose | 78.71 | 59.76 |
| Cytisine mesylate with lactose | 99.20 | 99.89 |
| Cytisine gentisate with lactose | 96.67 | 97.45 |

The invention is further defined with reference to the following claims.

The invention claimed is:

1. A gentisate salt of cytisine.

2. A solvate or hydrate of a gentisate salt according to claim 1.

3. A method for making a gentisate salt of cytisine, the method comprising:
   (i) preparing a first solution, of an acid salt former, of gentisic acid;
   (ii) preparing a second solution, of cytisine;
   (iii) adding said first solution of the acid salt former to said second solution of cytisine;
   (iv) maintaining a solution obtained in step (iii) at an elevated temperature for a fixed period of time;
   (v) allowing the solution to cool to ambient temperature;
   (vi) filtering the cooled solution; and
   (vii) drying the obtained solids.

4. A pharmaceutical composition comprising a gentisate salt according to claim 1, or a solvate or hydrate thereof, and a pharmaceutically acceptable carrier.

5. A pharmaceutical composition according to claim 4, wherein the pharmaceutically acceptable carrier is selected from lactose, corn starch, wheat starch, microcrystalline cellulose, or a mixture thereof.

6. A pharmaceutical composition according to claim 4, wherein the composition is a unit dosage form.

7. A pharmaceutical composition according to claim 4, wherein the composition is in a form of a tablet or capsule.

8. A method of treating nicotine addiction in a subject, said method comprising administering to said subject an effective amount of a gentisate salt according to claim 1 or a solvate or hydrate thereof.

9. The method of claim 8, wherein the salt or solvate or hydrate thereof, is administered in a composition comprising a pharmaceutically acceptable carrier.

10. The method of claim 9, wherein the pharmaceutically acceptable carrier is selected from lactose, corn starch, wheat starch, microcrystalline cellulose, or a mixture thereof.

11. The method of claim 9, wherein the composition is a unit dosage form.

12. The method of claim 9, wherein the composition is in a form of a tablet or capsule.

* * * * *